United States Patent [19]

Koeneman

[11] 4,204,284
[45] May 27, 1980

[54] JOINT PROSTHESIS WITH CONTOURED PIN

[75] Inventor: James B. Koeneman, Erie, Pa.

[73] Assignee: Lord Corporation, Erie, Pa.

[21] Appl. No.: 852,181

[22] Filed: Nov. 16, 1977

[51] Int. Cl.² .............................................. A61F 1/24
[52] U.S. Cl. ....................................... 3/1.91; 403/224
[58] Field of Search .................. 3/1.91, 1.911, 1.912, 3/1.913, 17 R, 18, 22, 29, 30, 31, 32, 12, 12.2, 12.4; 403/224, 120, 225, 228, 203, 226, 220

[56] References Cited

U.S. PATENT DOCUMENTS

| | | | |
|---|---|---|---|
| 2,011,817 | 8/1935 | Littlefield | 403/224 X |
| 2,183,076 | 12/1939 | Kaiser | 3/6 |
| 2,692,392 | 10/1954 | Bennington et al. | 3/33 |
| 3,147,964 | 9/1964 | Wolf | 403/224 X |
| 3,467,421 | 9/1969 | Bentley | 403/203 |
| 3,480,972 | 12/1969 | Prahl | 3/33 |
| 3,593,342 | 7/1971 | Niebauer et al. | 3/1 |
| 3,707,006 | 12/1972 | Bokros et al. | 3/1 |
| 3,875,594 | 4/1975 | Swanson | 3/1 |
| 3,916,451 | 11/1975 | Buechel et al. | 3/1.91 |
| 3,990,116 | 11/1976 | Fixel et al. | 3/1.91 |
| 4,038,705 | 8/1977 | Owens et al. | 3/2 |

*Primary Examiner*—Clifford D. Crowder
*Attorney, Agent, or Firm*—Maurice R. Salada; Lawrence R. Oremland

[57] ABSTRACT

A joint prosthesis comprises two relatively inextensible primary components that are spaced apart from one another. Disposed between and spaced from each of the primary components is a pivot member that is also fabricated of relatively inextensible material. When viewed in section taken normal to its central longitudinal axis, the pivot member has two discrete arcuate surfaces that are spaced apart from one another about the circumference of the pivot member. One of the primary components of the prosthesis is resiliently secured to one of the arcuate surfaces of the pivot member, while the other primary component of the prosthesis is resiliently secured to the other arcuate surface of the pivot member. The resilient connections between the pivot member and the primary components permit relative rotation between the pivot member and each of the primary components. As a result, the two primary components can rotate toward and away from each other about an axis that is disposed at least adjacent to and at least approximately parallel to the longitudinal axis of the pivot member. The resilient connections between the arcuate surfaces of the pivot member and the primary components of the prosthesis are preferably accomplished through the use of bodies of elastomeric material. Adjacent the spaced apart arcuate surfaces of the pivot member, the bodies of elastomer have greater circumferential dimensions that the arcuate surfaces so as to reduce stresses occurring at the elastomer-to-pivot member interfaces.

12 Claims, 4 Drawing Figures

JOINT PROSTHESIS WITH CONTOURED PIN

RELATED APPLICATIONS

The invention described, illustrated, and claimed in the present application is similar in structure and function to the joint prostheses described, illustrated, and claimed in commonly owned, concurrently filed application Ser. No. 852,183 of Leonard J. Schwemmer, entitled, "Joint Prosthesis," in commonly owned, concurrently filed application Ser. No. 852,111 of James B. Koeneman, entitled, "Knee Joint Prosthesis," and in commonly owned, concurrently filed joint application Ser. No. 852,182 of Leonard J. Schwemmer and Howard T. Wilson, entitled, "Ankle Joint Prosthesis."

BACKGROUND OF THE INVENTION

Resilient materials, such as elastomers, have long been used in external prosthetic devices for the human body to cushion impact or shock loads. Because impact loads are necessarily and regularly encountered in walking, two common prosthetic devices that have often incorporated resilient materials are artificial feet and ankle joint prostheses for use with artificial feet. In early designs, an ankle joint prosthesis was typically a metallic pivot that included a plain (e.g., sleeve) bearing or a rolling element (e.g., ball) bearing. Resilient or elastomeric material was disposed both about the pivot to help limit its motion and in various portions of an associated artificial foot to cushion or absorb impact loads. Typical combinations of a cushioned artificial foot and an ankle joint prosthesis that incorporates a metal-on-metal pivot are described and illustrated in Ehle U.S. Pat. Nos. 487,697, Rowley 1,090,881, and Kaiser 2,183,076.

Later in the development of ankle joint prostheses for external use, resilient or elastomeric material came to be utilized in such prostheses for properties other than its ability to absorb or cushion impact loads. In Desoutter U.S. Pat. No. 1,911,440, for example, a tubular rubber bushing is secured between a pin and a metal sleeve that circumscribes the pin to form a pivot for an ankle joint prosthesis. The outer sleeve is connected to an artificial foot, while the pin is connected to an artificial lower leg. Articulation is permitted by torsional deflection of the bushing. Because of the resilience of the bushing material, the ankle joint prosthesis automatically returns to a preselected position after it is deflected. The prosthesis also does not require lubrication because the bushing separates the adjacent metal surfaces of the pin and the sleeve. Similar ankle joint prostheses that employ a tubular bushing or body of elastomer between an outer rigid sleeve and an inner pin or sleeve are described and illustrated in Burger et al U.S. Pat. No. 2,605,475 and Prahl U.S. Pat. No. 3,480,972.

A pivot or pivotable assembly that incorporates a relatively thin, tubular body of elastomer secured between a pin and a larger diameter sleeve is only capable of extensive rotational movement about a single axis. In a typical ankle joint prosthesis, such as the Desoutter and Prahl ankle joint prostheses, such an elastomeric pivot is oriented generally perpendicular to the longitudinal axis of the wearer's leg and transverse to the longitudinal axis of the wearer's artificial foot. In the orientation that has been described, the elastomeric pivot permits extensive flexion in the dorsal and planter directions. An elastomeric pivot so oriented, however, can only provide a limited degree of inversion and eversion of a foot about its longitudinal axis or a parallel axis and only a limited degree of internal and external rotation of the foot about the longitudinal axis of the lower leg. The motions other than flexion are all accommodated primarily through compression of the elastomeric bushing, which is relatively thin and cannot afford any significant degree of deflection. To overcome some of the motion limitations inherent in the ankle joint prostheses of the Desoutter and Prahl patents, the ankle joint prosthesis of the previously mentioned Burger et al patent incorporates two elastomeric pivots disposed at right angles to each other. The Burger et al ankle joint prosthesis thus can resiliently permit both extensive dorsal and plantar flexion and extensive inversion and eversion. Other external ankle joint prostheses attempt to provide the three types of movement afforded by a natural ankle joint through the use of relatively massive blocks of elastomer, rather than the tubular bushings discussed above. The blocks of elastomer may be specially shaped or contoured in order to provide appropriate stiffnesses or motion capabilities in the three critical rotational directions. Examples of external ankle joint prostheses that incorporate large blocks of elastomer are described and illustrated in Bennington et al U.S. Pat. No. 2,692,392 and Asbelle et al U.S. Pat. No. 3,982,280.

Although resilient materials, and particularly elastomeric materials, have for many years been suggested for use in external joint prostheses, the use of resilient or elastomeric materials in internal joint prostheses has only recently been proposed. The apparent delay in the appearance of proposals for the use of resilient or elastomeric materials internally of the human body is probably attributable in part to the lack of a physiologically inert elastomeric material that could safely be used in the body. Nonetheless, with the development of suitable elastomeric materials, such as Dow Corning Corporation's Silastic ® silicone elastomer, a number of surgically implantable, elastomeric joint prostheses have been proposed, particularly for finger joints. The finger joint prostheses, in particular, tend to be entirely formed of elastomer or nearly so. Unfortunately, such designs require the elastomer to be bent of flexed extensively at some point to provide a pivot. The result is alternating tension and compression loading of the elastomer, which is detrimental to its long-term fatigue life. The use of notches in the elastomer to locate the pivot point further adds to the stresses in the elastomer. Examples of finger joint prostheses that are entirely formed of elastomer or nearly so are described and illustrated in Swanson U.S. Pat. Nos. 3,462,765, Niebauer et al 3,593,342, Lynch 3,681,786, and Swanson 3,875,594. Other than the finger joint prostheses mentioned above, relatively few implantable prostheses that employ resilient or elastomeric material have been identified. Nonetheless, the use of elastomeric material in an implantable hip joint prosthesis is suggested in Buechel et al U.S. Pat. No. 3,916,451, particularly FIG. 1, and in Bokros et al U.S. Pat. No. 3,707,006, particularly FIG. 5.

The ankle joint prostheses described in the previously mentioned patents to Desoutter, Burger et al and Prahl appear to represent the best presently known designs for use of the desirable properties of elastomeric material in a prosthesis that accommodates pivotal or rotational motion. Nonetheless, the elastomeric pivots that are incorporated in the ankle joint prostheses of these three patents do not make optimal use of elastomeric material within the space provided. In particular, the relatively thin, tubular bodies of elastomer in the ankle joint prostheses of Desoutter, Burger et al, and Prahl are subjected to relatively high, torsionally-induced strains which, over periods of extended use, will lead to failure of the elastomeric bodies. While the strains experienced by the elastomeric bodies of the patented ankle joint prostheses may not be detrimental in terms of a few hundred or even a few thousand articulations of the prostheses, the strains are critical when one considers several million articulations or deflections of the prostheses. Such numbers of articulations may easily be experienced during a year or two of normal use. In an ankle joint prosthesis that is used externally of the human body, replacement of the elastomeric elements of the prosthesis may merely represent additional expense and some inconvenience to the user. If such a joint prosthesis were implanted in the body of the user, on the other hand, failure of the elastomeric elements within one or two years would seriously limit the desirability of using such a prosthesis.

SUMMARY OF THE INVENTION

The present invention relates to a joint prosthesis for either internal or external use which incorporates resilient material to facilitate rotational movement and which utilizes the material in a configuration that will promote a long service life for the prosthesis. The invention is more particularly directed to a pin or pivot member for use in such a joint prosthesis. The pivot member has a specially configured outer circumference to reduce stress concentrations in selected areas of the prosthesis so as to increase the expected service life of the prosthesis. A joint prosthesis with a contoured pin according to the present invention comprises a pair of relatively inextensible primary components that are spaced apart from one another. Disposed between and spaced from each of the primary components is a relatively inextensible pin or pivot member. The pivot member has a central axis and, when viewed in section taken normal to the axis, has two discrete arcuate surfaces that are spaced apart from one another about the circumference of the pivot member. The pivot member is also resiliently secured to each of the two primary components of the prosthesis. The resilient securing structure includes a first portion that secures one of the primary components of the prosthesis to one of the arcuate surfaces of the pivot member and a second portion that secures the other primary component of the prosthesis to the other arcuate surface of the pivot member. The two portions of the securing structure resiliently permit and accommodate relative rotation or pivotal motion between the pivot member and each of the primary components of the prosthesis. As a result, the two primary components can rotate toward and away from each other about an axis that is disposed at least adjacent to and at least approximately parallel to the central axis of the pivot member. The two discrete arcuate surfaces of the pivot member facilitate attachment of the securing structure to the pivot member with a minimum of stress at the interfaces between the pivot member and the securing structure.

In a preferred embodiment of the invention, the two portions of the securing structure that are attached to the two discrete arcuate surfaces of the pivot member are at least partially formed of elastomer. Adjacent its interface with an arcuate surface of the pivot member, each of the two portions of the securing structure has a width measured circumferentially of the pivot member which is greater than a corresponding width of the adjacent arcuate surface of the pivot member. The two resilient portions of the securing structure may thus contact and be secured to portions of the circumference of the pivot member other than the two spaced apart arcuate surfaces. The benefits to be obtained from attaching the securing structure to portions of the circumference of the pivot member other than its spaced apart arcuate surfaces are greatest if the discrete arcuate surfaces of the pivot member are disposed at larger radial distances from the central axis of the pivot member than any other portion of the circumference of the pivot member, throughout at least a majority of its length. The two portions of the securing structure can then extend radially inwardly of the pivot member beyond its discrete arcuate surfaces, rather than terminating abruptly at the arcuate surfaces. Continuing the resilient securing material beyond the arcuate surfaces of the pivot member reduces or alleviates the high stresses that would otherwise be developed at the bond interface between the resilient material and each arcuate surface of the pivot member. Such stresses are particularly high when the resilient mateial is being deflected to accommodate relative rotation between the pivot member and the primary components of the prosthesis.

BRIEF DESCRIPTION OF THE DRAWING

For better understanding of the invention, reference may be made to the following description of an exemplary embodiment, taken in conjunction with the figures of the accompanying drawing, in which.

DESCRIPTION OF EMBODIMENT

Figure 1:
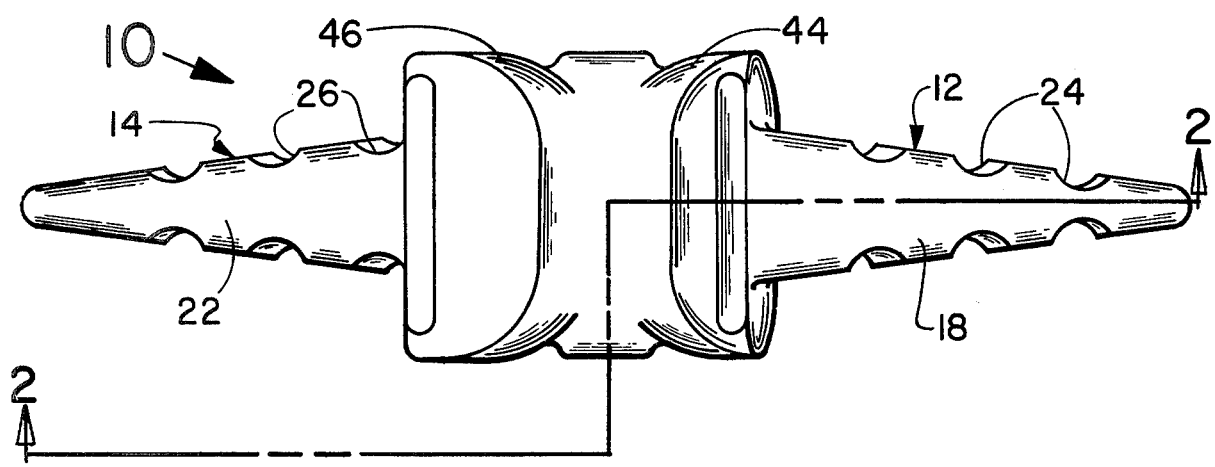
FIG. 1 is a plan view of a finger joint prosthesis according to the present invention.
Figure 2:
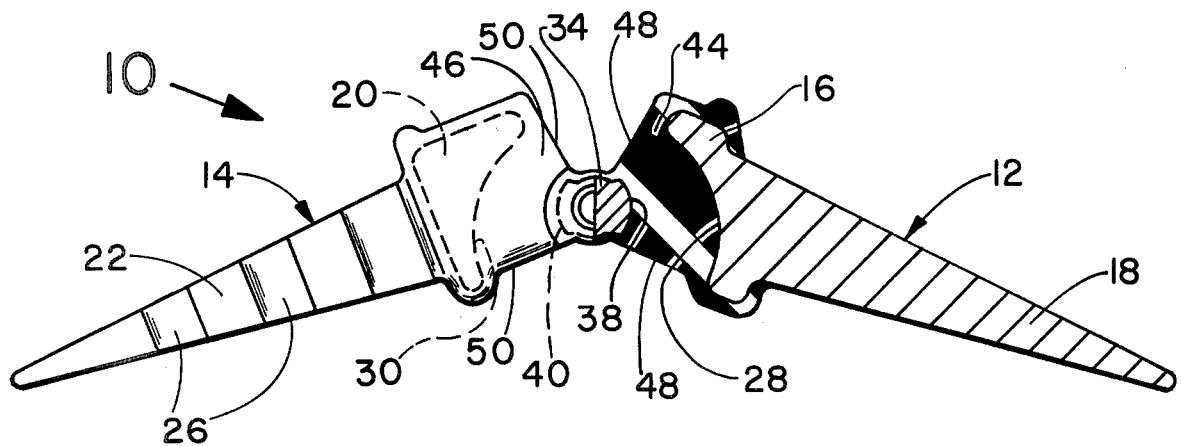
FIG. 2 is a side view, partly in section, of the finger joint prosthesis of FIG. 1, taken along line 2—2 of FIG. 1.
Figure 3:
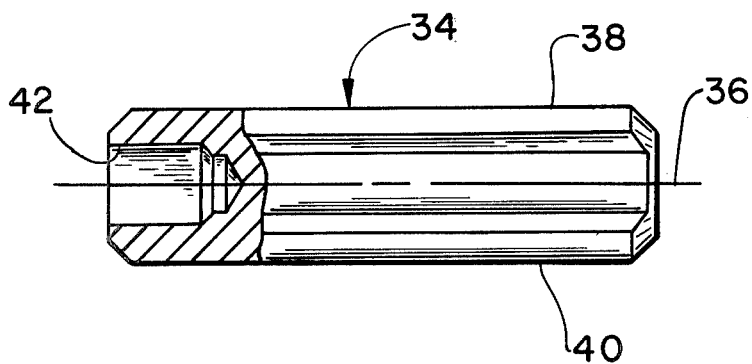
FIG. 3 is a side view, on an enlarged scale and partly in section, of the pin of the joint prosthesis shown in FIGS. 1 and 2.

FIG. 1 of the drawing illustrates, in plan view, a finger joint prosthesis 10 according to the present invention. The finger joint prosthesis 10 includes a proximal component 12 and a distal component 14 which are spaced apart from each other. Both the proximal component 12 and the distal component 14 are formed of a relatively inextensible and biocompatible material. Suitable materials include high density polyethylene, polyester, nylon, rigid silicone resins, stainless steel, cobalt-chromium alloys, titanium, and titanium alloys. The relative inextensibility of the materials is to be judged in comparison to the resilient material that is incorporated into the prosthesis 10. The proximal component 12 of the finger joint prosthesis 10 includes a head portion 16 and a stem or shank portion 18, as best shown in FIG. 2. The distal component 14 of the prosthesis 10 likewise includes a head portion 20 and a stem portion 22. The stem portions 18 and 22 of the two components 12 and 14 are tapered for axial insertion into adjacent phalanges or digital bones. Slots 24 and 26 are formed in the surfaces of the stem portions 18 and 22, respectively, in order to enhance the mechanical engagement between the two stem portions and the bone cement that is normally used to secure prostheses in the bones of the human body. The head portions 16 and 20 of the proximal and distal components 12 and 14, respectively, are fixed to the broad or wide ends of the stem portions 18 and 22 and may each be fabricated, as in the prosthesis 10, in one piece with a corresponding stem portion. The head portions 16 and 20 are also considerably wider than the adjacent ends of the stem portions 18 and 22 and each head portion presents an arcuate surface 28 or 30 to the other. As best seen in FIG. 2, the surfaces 28 and 30 of the head portions 16 and 20, respectively, are concavely arcuate when viewed in section taken along the longitudinal axes of the two components 12 and 14.

Figure 4:
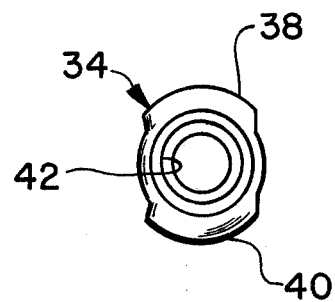
FIG. 4 is an end view of the pin shown in FIG. 3.

Disposed between the proximal and distal components 12 and 14 of the prosthesis 10 is a pin or pivot member 34. The pin 34 is formed of a relatively inextensible material, such as the materials from which the two primary components 12 and 14 of the prosthesis 10 may be formed. The positioning of the pin 34 with respect to the primary components 12 and 14 of the prosthesis 10 is such that the center of the pin is displaced from the intersection of the longitudinal axes of the primary components. In other words, as viewed in FIG. 2, the pin 34 lies below the point at which the extended longitudinal axis of the component 12 would intersect the extended longitudinal axis of the component 14. Such a positioning of the pin 34 locates the center of rotation or pivotal motion for the prosthesis 10 so as to simulate more closely the functioning of a natural finger joint. As best shown in FIG. 4, the pin 34 has, when viewed in section taken perpendicular to its central longitudinal axis 36, a pair of discrete and convexly arcuate circumferential surfaces 38 and 40. The two surfaces 38 and 40 are spaced apart about the circumference of the pin 34 and extend along the length of the pin. The surfaces 38 and 40 are also disposed at greater radial distances from the central axis 36 of the pin 34 than any of the remainder of the circumference of the pin, except perhaps at the ends of the pin. At opposite ends of the pin 34, the circumferential surfaces of the pin, including the surfaces 38 and 40, are all beveled to avoid sharp, right-angle corners that might produce stresses and weaknesses in bonds between the surfaces 38 and 40, for example, and adjacent bodies of resilient material. Each of the ends of the pin 34 also has formed in it a blind bore 42 that extends part way along the central longitudinal axis 36 of the pin. The bores 42 are intended to receive pins or lugs to hold the pin 34 in place in a mold as resilient material is introduced into the mold and cured about the pin to form the prosthesis 10.

In the prosthesis 10, the convexly arcuate surface 38 of the pin 34 is presented to the concavely arcuate surface 28 of the head portion 16 of the proximal component 12. The convexly arcuate surface 40 of the pin 34 is similarly presented to the concavely arcuate surface 30 of the head portion 20 of the distal component 14. The pin 34 is secured to the proximal and distal components 12 and 14 by a mass of resilient material, such as an elastomer, that is essentially separated into two distinct portions or bodies 44 and 46. The material used in the resilient bodies 44 and 46 must be biocompatible, as are certain grades of Dow Corning Corporation's Silastic ® silicone elastomer. The body of resilient material 44 extends between and is bonded to the concavely arcuate surface 28 of the head portion 16 of the proximal component 12 and the convexly arcuate surface 38 of the pin 34. The resilient body 46 extends between and is bonded to the concavely arcuate surface 30 of the head portion 20 of the distal component 14 and the convexly arcuate surface 40 of the pin 34. Each of the resilient bodies 44 and 46 has a pair of exposed surfaces 48 or 50 that extend lengthwise of the pin 34 and outwardly from adjacent the circumference of the pin in a generally radial direction. The exposed surfaces 48 of the resilient body 44 are spaced throughout their lengths, as measured generally radially of the axis 36, from the adjacent surfaces 50 of the resilient body 46. The surfaces 48 actually diverge from the surfaces 50 with increasing radial distance from the axis 36. As a result, deflection of the resilient body 44, for example, to permit relative rotation between the proximal component 12 and the pin 34 will not interfere, at least initially, with similar rotational movement between the distal component 14 and the pin.

Adjacent each of the arcuate surfaces 28 and 38, the resilient body 44 has a circumferential width, or a width measured generally along the curve of the surface and about the axis 36, that is greater than the corresponding width of the adjacent surface 28 or 38. The material in the resilient body 44 passes around the edges of the surface 28, for example, and along the sides of the head portion 16 of the component 12 so as totally to encapsulate the head portion 16. Similarly, the material in the resilient body 44 passes radially inwardly beyond the arcuate surface 38 of the pin 34 and over other portions of the circumference of the pin. Adjacent each of the arcuate surfaces 30 and 40, the resilient body 46 has a circumferential width that is greater than the corresponding width of the surface 30 or 40. Like the resilient body 44, the resilient body 46 totally encapsulates the head portion 20 of the adjacent primary component 14 of the prosthesis 10. The material of the resilient body 46 also passes radially inwardly beyond the arcuate surface 40 of the pin 34 to other portions of the circumferential surface of the pin. Together, the bodies of resilient material 44 and 46 extend over and are bonded to all of the circumference of the pin 34 so as totally to encapsulate the pin, except for its ends. By continuing the resilient material of the bodies 44 and 46 beyond the arcuate surfaces 28, 38, 30, and 40 to other surfaces of the inextensible elements 12, 14, and 34 of the prosthesis 10, high stresses adjacent the bonded interfaces between the resilient bodies and the arcuate surfaces are diminished. Such stresses are particularly large when the resilient bodies 44 and 46 are deflected to permit rotation to occur between the components 12 and 14 of the prosthesis 10 and the pin 34 of the prosthesis. Stress concentrations are also alleviated by the provision of rounded corners at the junctures of the various surfaces on the head portions 16 and 20 of the proximal and distal components 12 and 14 of the prosthesis 10.

In operation, when implanted in a finger, for example, the prosthesis 10 permits considerable flexion and extension between proximal and distal phalanges. In other words, the prosthesis 10 permits extensive pivoting motion between two digital bones, and between the two components 12 and 14 of the prosthesis which are implanted in the bones, about an axis that is at least adjacent to and at least approximately parallel to the longitudinal axis 36 of the pin 34, if not coincident with the axis 36. Relative pivotal motion or rotation between the proximal component 12 and the pin 34 will be accommodated by resilient shearing deflection of the body 44. When deflected, the resilient body 44 will also provide a resilient restoring force to return the component 12 and the pin 34 to their initial relative positions. Relative pivotal motion or rotation between the distal component 14 and the pin 34 will be accommodated by similar resilient shearing deflection of the body 46, which will also offer a resilient restoring action when deflected. The flexural motions will be actuated by the muscles and tendons of the finger, which will not be displaced or destroyed during implantation of the prosthesis 10. As is apparent in FIG. 2, the stem portions 18 and 22 of the two components 12 and 14 of the prosthesis 10 are normally disposed at an angle other than 180° with respect to each other about the axis 36. This predeflection of the two components 12 and 14 facilitates implantation of the prosthesis 10 into a finger, simulates the natural, slightly curved position assumed by the digits of the human hand in its relaxed position, and avoids having to deflect either of the resilient elements 44 and 46 entirely in one direction to achieve the maximum desired range of flexural movement of the digits. A similar predeflection of the major components of a finger joint is described and illustrated in Fixel et al U.S. Pat. No. 3,990,116.

The resilient bodies 44 and 46 that interconnect the pin 34 and the primary components 12 and 14 of the prosthesis 10 may be deflected to afford limited pivotal or rotational movements between the components 12 and 14 about axes generally perpendicular to the axis 36. In proximal and distal interphalangeal joints, such additional rotational movements may not be desirable. In metacarpal-phalangeal joints, on the other hand, the ability of the prosthesis to accommodate pivotal motions about other axes is desirable. The degree of motion that may be afforded about axes other than the axis 36 may be changed by adjusting the length of the pin 34, changing the thickness of the resilient bodies 44 and 46 as measured generally radially of the pin 34, or by shaping the pin to have arcuate surfaces along its length. Shortening the pin 34 will increase the motion permitted about the other axes, while lengthening the pin will decrease the motion permitted. Curving the pin 34 along its length will increase the degree of motion afforded about axes other than the axis 36. In a pin 34 that is curved along its length, the surfaces 38 and 40 are arcuate not only in planes perpendicular to the longitudinal axis 36 of the pin 34, but also in planes parallel to and passing through the axis 36. If necessary, the longitudinal curvature could be such that the pin 34 would approximate a spherical shape.

The resilient bodies 44 and 46 of the prosthesis 10 are illustrated as being entirely formed of elastomer, for example. Nonetheless, it would be possible to insert into each of the bodies of resilient material 44 and 46 one or more shims or plates fabricated of a relatively inextensible material and configured to conform to the opposed surfaces 28 and 38 and 30 and 40 to which the resilient bodies are bonded. Such shims or plates would increase the compressive load carrying capability of the resilient elements 44 and 46 by restricting the ability of the resilient material to bulge or deflect along its free surfaces, such as surfaces 48 and 50.

It will be understood that the embodiment described above is merely exemplary and that persons skilled in the art may make many variations and modifications without departing from the spirit and scope of the invention. Thus, for example, although the embodiment of the invention described above is an internal finger joint prosthesis, the invention could equally well be embodied in prostheses for internal use to replace other joints of the body and in prostheses intended for use outside the body. All such modifications and variations are intended to be within the scope of the invention as defined in the appended claims.

What is claimed is:

1. A joint prosthesis comprising:
   (a) a first relatively inextensible component;
   (b) a second relatively inextensible component that is spaced from the first component along a first axis;
   (c) means defining a relatively inextensible pivot member disposed between and spaced from each of the first and second components, the pivot member having a central axis which is oriented generally perpendicular to said first axis, the first and second components being disposed entirely on opposite sides of and separated by a plane oriented generally perpendicular to said first axis and generally parallel to said central axis of the pivot member, the pivot member also having, when viewed in section taken normal to said central axis, two discrete arcuate surfaces spaced apart from one another about the circumference of the pivot member and connecting surfaces disposed between said discrete arcuate surfaces, said connecting surfaces being within the generatrix of at least one of said discrete arcuate surfaces; and
   (d) means for resiliently securing the pivot member to each of the first and second components, the securing means including (i) a first portion that secures the first component to one of the arcuate surfaces of the pivot member and (ii) a second portion that secures the second component to the other of the arcuate surfaces of the pivot member, each of the first and second portions of the securing means extending about the junctions of said discrete arcuate surfaces and said connecting surfaces and having at least one exposed surface that extends outwardly from adjacent the pivot member, said at least one exposed surface of the first portion of the securing means being spaced from said at least one exposed surface of the second portion of the securing means throughout at least a majority of their respective lengths measured generally radially of said central axis of the pivot member,
   the first and second components being coupled to each other only through the pivot member and the first and second portions of the securing means, the relative inextensibility of the first and second components and the pivot member being determined in comparison to the securing means, the first and second portions of the securing means deflecting in torsional shear to accommodate relative rotation between the pivot member and each of the first and second components so that the first and second components can move toward and away from each other in directions generally parallel to said first axis through frotation about a second axis that is disposed at least adjacent to and at least approximately parallel to the central axis of the pivot member.

2. A joint prosthesis, according to claim 1, wherein the arcuate surfaces of the pivot member extend lengthwise of the pivot member and are disposed generally opposite one another about the circumference of the pivot member.

3. A joint prosthesis, according to claim 1, wherein the central axis of the pivot member is a central longitudinal axis.

4. A joint prosthesis, according to claim 1, wherein the two arcuate surfaces of the pivot member are disposed at greater radial distances from the central axis of the pivot member than any other portion of the circumference of the pivot member throughout at least a majority of the length of the pivot member.

5. A joint prosthesis, according to claim 4, wherein each of the first and second portions of the securing means is at least partially formed of elastomer and has a width measured (i) circumferentially of the pivot member and (ii) adjacent an arcuate surface of the pivot member which is greater than a corresponding width of said adjacent arcuate surface of the pivot member, the first and second portions of the securing means contacting and being secured to portions of the circumference of the pivot member other than its two arcuate surfaces.

6. A joint prosthesis, according to claim 1, wherein each of the first and second components includes a surface that is concavely arcuate in shape when viewed in section taken generally normal to the central axis of the pivot member, and wherein each of the two arcuate surfaces of the pivot member is convexly arcuate, each of the concavely arcuate surfaces of the first and second components being presented to and spaced from a convexly arcuate surface of the pivot member.

7. A joint prosthesis, according to claim 1, wherein each of the first and second components includes a stem for attachment to a skeletal bone, the stem of each component being disposed generally opposite and extending away from the pivot member and the other component.

8. A joint prothesis, according to claim 1, wherein the pivot member is connected to the first and second components only through the first and second portions of the securing means.

9. A joint prosthesis comprising:
(a) a first relatively inextensible component having a first surface that is concavely arcuate in shape;
(b) a second relatively inextensible component which is spaced from the first component along a first axis and which has a second surface that is concavely arcuate in shape;
(c) means defining a relatively inextensible pivot member disposed between and spaced from each of the first and second components, the pivot member having a central longitudinal axis which is oriented generally perpendicular to said first axis, the first and second components being disposed entirely on opposite sides of and separated by a plane oriented generally perpendicular to said first axis and generally parallel to said central longitudinal axis of the pivot member, the pivot member also having, when viewed in section taken normal to said central longitudinal axis, two discrete, convexly arcuate surfaces spaced from one another about the circumference of the pivot member, the two spaced apart arcuate surfaces of the pivot member being disposed at greater radial distances from the central longitudinal axis of the pivot member than any other portion of the circumference of the pivot member throughout at least a majority of its length, the spaced apart convexly arcuate surfaces of the pivot member also being presented to and spaced from the first and second concavely arcuate surfaces; and
(d) means for resiliently securing the pivot member to each of the first and second components, the securing means including (i) a first portion which is at least partially formed of elastomer and which secures the first concavely arcuate surface to one of the two convexly arcuate surfaces of the pivot member and (ii) a second portion which is at least partially formed of elastomer and which secures the second concavely arcuate surface to the other of the two convexly arcuate surfaces of the pivot member, each of the first and second portions of the securing means extending circumferentially about said pivot member and beyond their respective discrete arcuate portions and having at least one exposed surface that extends outwardly from adjacent the pivot member, said at least one exposed surface of the first portion of the securing means being spaced from said at least one exposed surface of the second portion of the securing means throughout at least a majority of their respective lengths measured generally radially of said central longitudinal axis of the pivot member,
the first and second components being coupled to each other only through the pivot member and the first and second portions of the securing means, the relative inextensibility of the first and second components and the pivot member being determined in comparison to the elastomer of the securing means, the first and second portions of the securing means deflecting in torsional shear to accomodate relative rotation between the pivot member and each of the first and second components so that the first and second components can move toward and away from each other in directions generally parallel to said first axis through rotation about a second axis that is disposed at least adjacent to and at least approximately parallel to the central longitudinal axis of the pivot member.

10. A joint prosthesis, according to claim 9, wherein each of the first and second portions of the securing means has a width measured (i) circumferentially of the pivot member and (ii) adjacent a convexly arcuate surface of the pivot member which is greater than a corresponding width of said adjacent arcuate surface of the pivot member, the first and second portions of the securing means contacting and being secured to portions of the circumference of the pivot member other than its two convexly arcuate surfaces.

11. A joint prosthesis, according to claim 10, wherein each of the first and second portions of the securing means has a pair of exposed surfaces, each exposed surface extending generally lengthwise of the pivot member and outwardly from adjacent the pivot member, the exposed surfaces of the first portion of the securing means being spaced from the exposed surfaces of the second portion of the securing means throughout at least a majority of their respective lengths measured generally radially of the central longitudinal axis of the pivot member.

12. A joint prosthesis for use in replacement of a joint in a human body comprising a first member adapted to be connected with a first portion of a human body, a second member adapted to be connected with a second portion of a human body, a pivot member disposed between the first and the second members, said pivot member having an outer periphery circumscribing a longitudinal central axis, said outer periphery comprising when viewed in section taken normal to said central axis first and second discrete arcuate surfaces and connecting surfaces disposed between said first and second arcuate surfaces, said connecting surfaces being within the generatrix of at least one of said first and second arcuate surfaces, securing means for resiliently connecting the pivot member to the first and second members for allowing said first and second members to rotate about said outer periphery of said pivot member and about axes parallel to said longitudinal central axis, said securing means including a first body of elastomeric material disposed between said first member and said first arcuate surface and a second body of elastomeric material disposed between said second member and said second arcuate surface, said first and second bodies of elastomeric material including respective extensions disposed circumferentially beyond their respective arcuate surfaces and extending toward each other, each extension disposed partially about a respective portion of connecting surface joining the first and second arcuate surfaces, said extensions of said first and second bodies of elastomeric material having respective side surfaces which are spaced from each other and which extend toward said one connecting surface to allow said first and second bodies of elastomeric material to deflect in torsional shear toward each other about said first and second arcuate surfaces while relieving stresses about the junctions of said first and second arcuate surfaces with the said one connecting surface.

* * * * *